US008184271B2

(12) United States Patent
Pittaro et al.

(10) Patent No.: US 8,184,271 B2
(45) Date of Patent: *May 22, 2012

(54) DIFFERENTIATION OF FLOW CYTOMETRY PULSES AND APPLICATIONS

(75) Inventors: Richard Pittaro, San Carlos, CA (US); Bruce Goldman, Redwood City, CA (US); Ray Lefebvre, Berkeley, CA (US); David A King, Menlo Park, CA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/951,911

(22) Filed: Nov. 22, 2010

(65) Prior Publication Data

US 2011/0063602 A1 Mar. 17, 2011

Related U.S. Application Data

(63) Continuation of application No. 11/862,680, filed on Sep. 27, 2007, now Pat. No. 7,847,923.

(60) Provisional application No. 60/848,200, filed on Sep. 29, 2006.

(51) Int. Cl.
*G01P 3/36* (2006.01)

(52) U.S. Cl. ...... 356/28; 356/28.5; 73/202.5; 73/204.11

(58) Field of Classification Search .................... 356/28, 356/28.5; 73/202.5, 204.11, 204.12, 204.13, 73/204.14

See application file for complete search history.

(56) References Cited

U.S. PATENT DOCUMENTS

| 3,638,488 | A | 2/1972 | Meijer |
| 3,938,038 | A | 2/1976 | Campbell |
| 4,021,117 | A | 5/1977 | Gohde et al. |
| 4,662,742 | A | 5/1987 | Chupp |
| 4,745,285 | A | 5/1988 | Recktenwald et al. |
| 5,561,515 | A | 10/1996 | Hairston et al. |
| 5,831,723 | A | 11/1998 | Kubota et al. |
| 6,075,611 | A | 6/2000 | Dussan et al. |
| 6,710,871 | B1 | 3/2004 | Goix |
| 7,268,859 | B2 | 9/2007 | Sage, Jr. et al. |
| 2002/0028434 | A1 | 3/2002 | Goix et al. |
| 2006/0021437 | A1 | 2/2006 | Kaduchak et al. |

FOREIGN PATENT DOCUMENTS

CA 2518882 A1 10/2004

OTHER PUBLICATIONS

Shapiro, "Pratical Flow Cytometry," 4th Ed., Willey, Hoboken, 2003.
Westo et al., "Doublet Discrimination in DNA Cell-Cycle Analysis," Cytometry, 2001, vol. 46, pp. 296-306.

(Continued)

*Primary Examiner* — Luke Ratcliffe
(74) *Attorney, Agent, or Firm* — Houst Consulting

(57) ABSTRACT

A method of analyzing pulses from a flow cytometer in which particles in a fluid pass through an excitation volume of an electromagnetic radiation and interact with the electromagnetic radiation to generate signals in the form of pulses includes generating a time-dependent pulse indicative of the characteristics of one or more particles passing through the excitation volume of the electromagnetic radiation, determining a measurement window by selecting a portion of the pulse with a starting point and an ending point above a predetermined value, and calculating a first derivative of the pulse with respect to time over the measurement window.

14 Claims, 12 Drawing Sheets

OTHER PUBLICATIONS

Savitzky et al., "Smoothing and Differentiation of Data by Simplified Least Squares Procedures," Analytical Chemistry, Jul. 1964, vol. 36, No. 8, pp. 1627-1639.

PCT, International Search Report (PCT/ISA/210) in PCT/US07/79761, Aug. 27, 2008, 2 pages.

PCT, Written Opinion of the International Searching Authority (PCT/ISA/237) in PCT/US07/79761, Aug. 27, 2008, 2 pages.

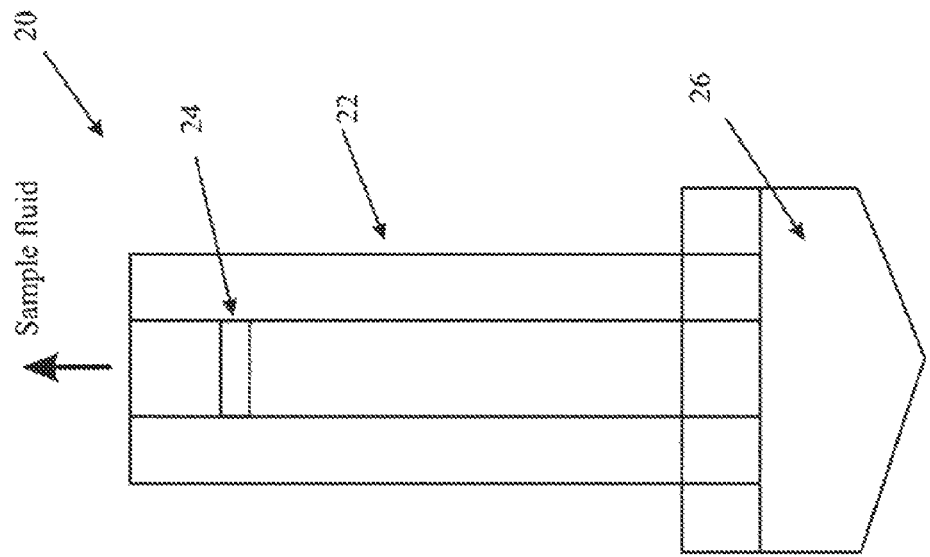
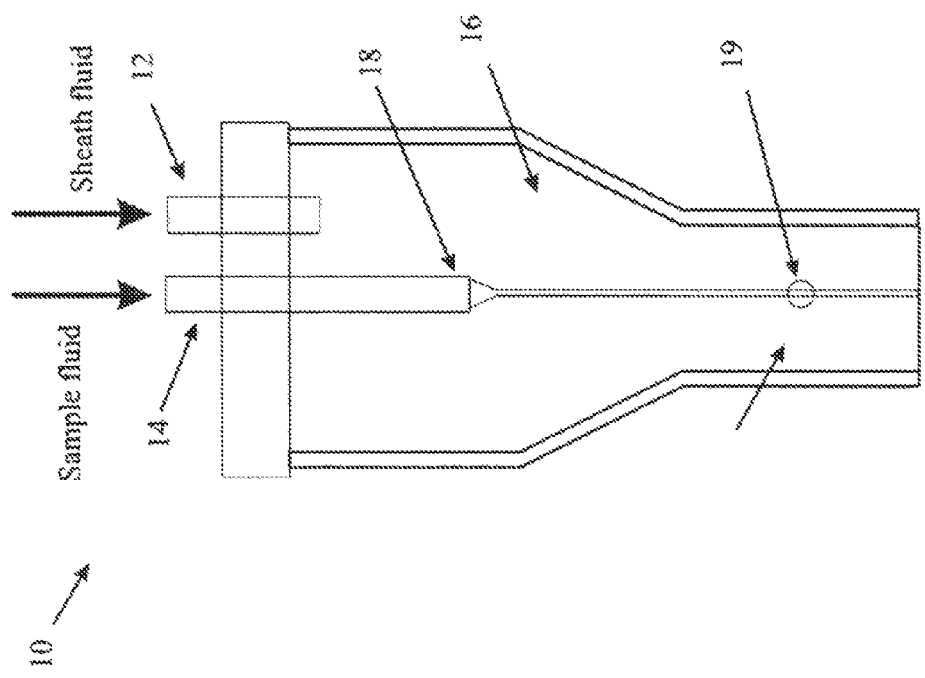
Fig. 1b
Fig. 1a

DIFFERENTIATION OF FLOW CYTOMETRY PULSES AND APPLICATIONS

CROSS-REFERENCE TO RELATED APPLICATIONS

This is a continuation of U.S. application Ser. No. 11/862,680 filed Sep. 27, 2007, which claims the benefit of priority under 35 USC §119(e) to U.S. Provisional Patent Application Ser. No. 60/848,200 filed Sep. 29, 2006, the disclosures of which are incorporated herein by reference.

TECHNICAL FIELD

This invention relates in general to flow cytometry and in particular to methods and apparatus for analyzing pulses produced by flow cytometers.

BACKGROUND

Flow cytometer systems are used to detect and count microorganisms and in varied applications throughout the life sciences including clinical diagnostics and immunology, protein and nucleic acid detection, hematology, and oncology. Commercially-available instruments range from complex laboratory systems that may be configured for a wide range of measurements to low-cost bench top systems with more limited capabilities. In the current biotechnology market, the price of a flow cytometer typically increases with its measurement precision and the number of different measurements it is capable of performing.

Flow cytometers are typically used to identify and count particles with specific characteristics in a fluid sample. As used herein, the term "particles" refers to, for example, latex spheres, bacteria, viruses, DNA fragments, cells, molecules, or constituents of whole blood. Particles may scatter excitation light directly or fluoresce when illuminated by light of an appropriate wavelength. In many cases, the fluorescent emission properties are optimized for specific measurements by attaching probe molecules to the entire particles or to microscopic structures within the particles.

In a typical flow cytometer, a particle-containing sample fluid flows through an excitation volume where the particles are illuminated by a focused light source. As they flow through the excitation volume, the particles scatter light out of the beam and fluoresce. In many cases, the fluorescent emission process is enhanced by bonding probe molecules to the particles or to structures within the particles. Particles are typically identified and counted by collecting and analyzing the light pulses that are emitted and scattered as the particles pass through the excitation volume.

Flow cytometers may be divided into two broad categories according to the composition of the fluid in and around the excitation volume. In sheath flow instruments, the fluid in the region of the excitation volume has two components: the particle-containing sample fluid and a particle-free sheath fluid that surrounds the sample fluid and confines it to a region near the flow axis. In capillary flow cytometers, the particle-containing sample fluid fills the entire flow volume and there is no sheath fluid.

Techniques for analyzing pulses produced by flow cytometers have been known and described for example in U.S. Pat. Nos. 4,021,117 and 3,938,038, the disclosures of which are incorporated herein by reference in their entirety.

SUMMARY

This invention provides a method of analyzing pulses from a flow cytometer in which particles in a fluid pass through an excitation volume of an electromagnetic radiation and interact with the electromagnetic radiation to generate signals in the form of pulses. In the method, a time-dependent pulse indicative of the characteristics of one or more particles passing through the excitation volume of the electromagnetic radiation is generated. A measurement window is determined by selecting a portion of the pulse with a starting point and an ending point above a predetermined value. A first derivative of the pulse with respect to time over the measurement window is calculated.

In one embodiment, the velocity of a particle passing through an excitation volume is calculated using the first derivative of the pulse. The measured value of the pulse is then corrected using the calculated velocity of the particle.

In another embodiment, the number of times (n) that the first derivative approximates a zero value within the measurement window is determined. The pulses are then differentiated using the determined number of times (n) that the first derivative approximates a zero.

In a further embodiment, this invention provides a method of analyzing pulses from a flow cytometer in which particles in a fluid pass through two or more excitation volumes partially defined by two or more electromagnetic radiation beams and interact with the two or more electromagnetic radiations to generate signals in the form of pulses. The method includes generating a first time-dependent pulse of a first particle passing through a first excitation volume in the capillary; calculating a first derivative of the first time-dependent pulse over a measurement window; calculating a first velocity of the first particle using the first derivative of the first time-dependent pulse; generating a second time-dependent pulse of a second particle passing through a second excitation volume in the capillary; calculating a second first derivative of the second time-dependent pulse over a measurement window; calculating a second velocity of the second particle using the second first derivative of the second time-dependent pulse; and correlating the first and second time-dependent pulses by comparing the calculated first and second velocity.

In one aspect, the invention provides an apparatus for analyzing particles. The apparatus comprises a capillary tube, a source of light, an optical system directing an electromagnetic radiation from the source of light to the capillary tube forming an excitation volume in the capillary tube, means for causing particles in a fluid to pass through the excitation volume in which the particles interact with the electromagnetic radiation to scatter light and/or emit fluorescent light, means for detecting the fluorescent light in the forms of pulses, and means for calculating a first derivative of the fluorescent light pulse with respect to time over a measurement window.

BRIEF DESCRIPTION OF THE DRAWINGS

These and various other features and advantages of the present invention will become better understood upon reading of the following detailed description in conjunction with the accompanying drawings and the appended claims provided below, where:

FIG. 1A is a schematic illustrating a flow cell in a sheath flow cytometer;

FIG. 1B is a schematic illustrating a flow cell in a capillary flow cytometer;

DETAILED DESCRIPTION OF VARIOUS EMBODIMENTS

Figure 2:
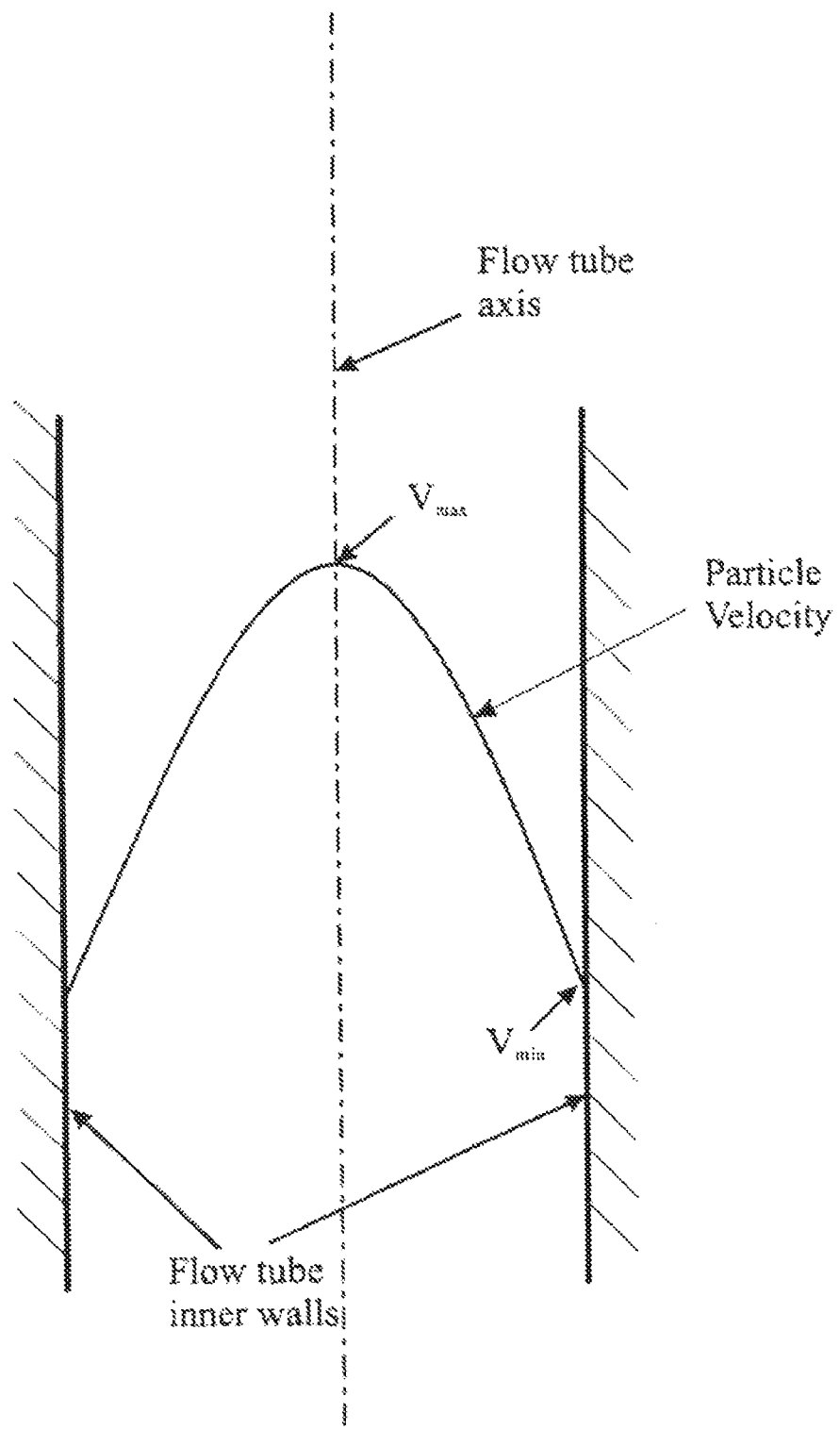
FIG. 2 is a schematic illustrating a stationary laminar flow condition in a flow cytometer.

Various embodiments of the invention are described hereinafter with reference to the figures. It should be noted that some figures are schematic and the figures are only intended to facilitate the description of specific embodiments of the invention. They are not intended as an exhaustive description of the invention or as a limitation on the scope of the invention. In addition, one aspect described in conjunction with a particular embodiment of the invention is not necessarily limited to that embodiment and can be practiced in any other embodiments of the invention.

FIGS. 1A-1B schematically illustrate representative flow cells for two cytometer systems that can be used to implement the method of the invention. In a sheath flow cell 10 shown in FIG. 1A, a sheath fluid enters the cell 10 through a pressurized inlet 12 and a sample fluid containing particles is injected into the cell 10 through a pressurized nozzle 14 (core injector). Between the cell inner wall and core injector 14 is formed a sheath fluid volume 16. In the region between the nozzle tip 18 and the excitation volume 19, the diameter of the cell 10 is gradually decreased in order to increase the velocity of the sheath fluid and decrease the sample fluid diameter. By way of example, the diameter of the sample fluid near the excitation volume 19 is between 5 to 50 microns while the diameter of the sheath fluid is equal to the cell diameter. By way of example, the flow cell has a diameter between 50 and 75 microns in the portion of the cell containing the excitation volume.

In a capillary flow cell 20 shown in FIG. 1B, a capillary tube 22 provides a substantially constant inner cross section that is filled with a sample fluid. The cross-sectional dimension of the sample fluid in the excitation region 24 is significantly larger than the cross-sectional dimension of the sample fluid excitation region 19 in a sheath flow system 10 and the flow velocities are comparatively smaller. By way of example, the inside edge dimension for a square flow cell 20 in a capillary flow cytometer is 100 microns. In operation, a sample fluid is drawn from a sample reservoir 26 through the excitation volume 24.

Sheath flow cells are significantly more complicated and expensive than capillary flow cells. Sheath flow cells have several advantages with respect to measurement precision. One advantage is that particles in the sample fluid travel through the excitation volume with an approximately constant velocity. In both cytometer systems, the flow velocity is adjusted to create a smooth laminar flow in the region of the cell containing the excitation volume and the radial velocity dependence is approximately parabolic. In a sheath flow cell, the sample fluid is confined to a narrow region surrounding the cell axis, thus effectively minimizing the variation in particle velocity. In contrast, in a capillary flow cell, particles traveling near the wall have a much smaller velocity than those traveling near the center of the cell, as illustrated in FIG. 2. By way of example, the velocities of the particles traveling at appreciable distance from the axis of a 100 micron square capillary cytometer flow cell are approximately 33% of the velocities of the particles traveling near the axis.

A sheath flow cell uses a small, centrally-located excitation volume. With a laser excitation source of fixed output power, the light intensity in a sheath flow cell is significantly greater than the intensity in a capillary flow instrument where the excitation volume fills the entire cell. In addition, the contribution of scattering and refraction from the cell walls is minimal and constant in magnitude in a sheath flow cell. In a capillary instrument, wall effects may be significant and vary in magnitude with the position of the emitting particle with respect to the cell axis.

Flow cytometers have been described in H. M. Shapiro, Practical Flow Cytometry, Wiley, Hoboken (2004), U.S. Pat. No. 4,662,742 to Chupp, U.S. Pat. No. 4,745,285 to Recktenwald et al., and U.S. Patent Application Publication No. 2002/0028434 A1, the disclosures of which are incorporated herein by reference in their entirety.

Figure 3:
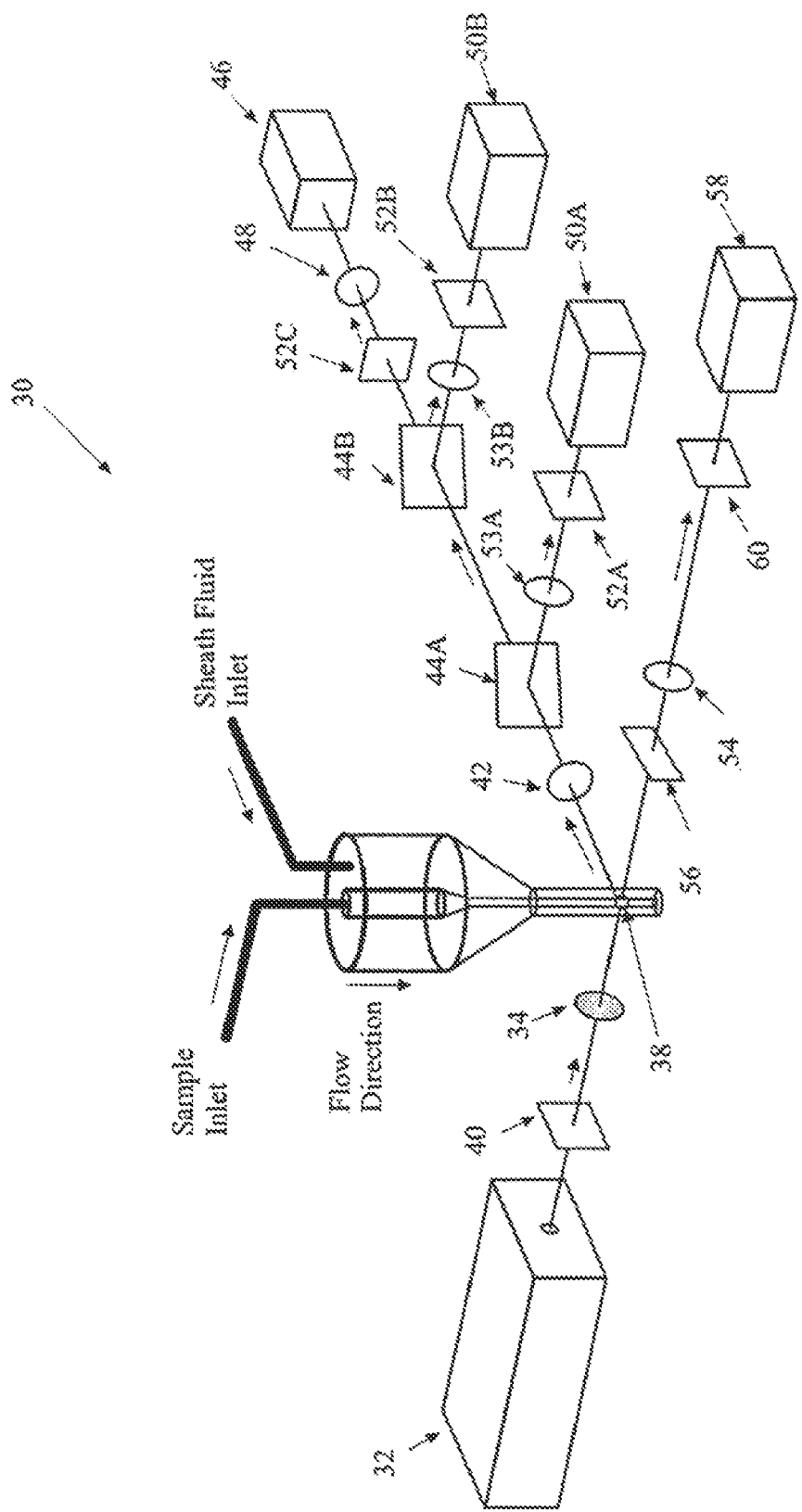
FIG. 3 is a schematic illustrating a sheath flow cytometer system.

FIG. 3 is a schematic representation of a sheath flow cytometer 30 that may be used to implement this invention. In this system, the excitation beam is generated by a light source 32 such as a laser, a laser-driven frequency nonlinear converter such as a frequency doubler, tripler or quadrupler, an optical parametric oscillator, a light-emitting diode (LED), a superluminescent diode, or an arc lamp.

An excitation optical system 34 focuses the excitation beam 36 into a flow cell 10 to define an excitation volume 38. The excitation optical system 34 is shown as a simple lens in FIG. 3 but may include one or more components such as diffractive optics, reflective optics and refractive optics. An optional bandpass filter 40 with high transmission at the excitation wavelength may be placed between the excitation light source 32 and the excitation volume 38 to block light emitted by the excitation source 32 at wavelengths different from the excitation wavelength.

The focused excitation light interacts with particles flowing through the excitation volume 38 via several physical processes including fluorescence excitation, absorption, small-angle scattering, and large-angle scattering. Particles may be identified and counted by measuring the wavelength, amplitude, duration and shape of the light pulses that are generated when they are illuminated by the excitation beam.

Scattered excitation light typically has an angular distribution that is determined by the size and shape of the scattering particles and is collected at large angles (>45 degrees) and small angles (<10 degrees) to the excitation beam propagation axis. Fluorescent light is typically emitted into all solid angles and is collected at large angles to the excitation beam propagation direction.

A maximum signal-to-noise ratio may be obtained by examining the fluorescent and scattered light pulses against a dark background. In large angle scatter and fluorescence measurements, the background light level is minimized by collecting light at large angles to the excitation beam propagation direction and using apertures to block non-particle sources of light. In forward scattering measurements, the background light level is typically minimized by blocking the excitation beam.

Returning to FIG. 3, a large-angle collection optical system 42 gathers fluorescent light and light that is scattered into a cone of angles around an axis that is orthogonal to the excitation beam propagation axis. Scattered light passes through the dichroic beamsplitters 44A, 44B and is focused onto the active element of the large angle scatter detector 46 by a lens or alternative focusing optical system 48. Fluorescent light of a first wavelength is reflected towards a first fluorescence detector 50A by the first dichroic beamsplitter 44A and fluorescent light of a second, different wavelength is reflected by the second dichroic beamsplitter 44B towards a second fluorescence detector 50B. Lens or alternative focusing optical system 53A and 53B are used to focus fluorescent light of first and second wavelength into fluorescence detector 50A and 50B respectively. One or more optical bandpass filters 52A, 52B, 52C may be placed between the excitation volume 38 and the detectors 46, 50A, 50B, to restrict the wavelengths reaching the detectors.

Fluorescent light is commonly emitted by probe molecules such as organic dye molecules that are attached to certain particles or specific structures within certain particles before they are introduced into the flow. Probe molecules are typically strong absorbers of excitation light that efficiently convert absorbed light energy to fluorescent emission. A red shift (or Stokes shift) of the fluorescent light wavelength with respect to the excitation light wavelength allows the fluorescent light to be separated from the excitation light with a conventional transmission filter or grating. Fluorescent photons are typically emitted within a few nanoseconds after the absorption of a photon from the excitation beam. This delay is short compared to the time required for a particle to travel through the excitation volume in a typical flow cytometer.

In certain applications, probe molecules with different emission and/or excitation spectra may be bonded to different types of sample particle or different structures within a single type of sample particle. By measuring the amplitude of the fluorescent light pulses at different wavelengths, it is possible to make simultaneous measurements on a single particle and/or differentiate signals that are produced by different particles or structures.

Light that is scattered at small angles to the excitation beam propagation axis may be collected by the forward scatter imaging system 54. A beam block 56 may be placed between the excitation volume 38 and the forward scatter imaging system 54 to prevent the unscattered excitation beam from reaching the forward scatter imaging system 54. Scattered light passing around the edges of the beam block 56 is collected and focused onto the active element of the forward scatter detector 58. A bandpass filter 60 may be inserted between the excitation volume 38 and the forward scatter detector 58 to transmit light at the excitation wavelength and block light at other wavelengths.

Scattered excitation light may be used to discriminate between different particle types. The amount of light that is scattered at small angles to the propagation axis of the excitation beam varies approximately with particle size while large angle scattering is a function of particle granularity. Certain particle species may be discriminated by measuring the ratio of small-angle to large-angle scattering.

Light pulses generated by the illuminated particles are separated according to emission angle and wavelength. Separation according to emission angle is accomplished by placing lenses with well-defined collection apertures at different angles with respect to the propagation of the excitation beam. Wavelength separation may be accomplished by passing the pulses through a series of dielectric bandpass and/or edge filters.

After collection and color separation, light pulses are converted to analog electronic pulses by photomultipliers or photodiodes. A data acquisition system converts the analog signals to digital data for subsequent analysis by a digital signal processor or computer.

The shape and amplitude of the light pulses reaching the detectors are determined by the optical properties of the particles, the particle velocities, and their position relative to the axes of the collection optical systems. The optical properties of the particles are determined by their size, shape, and transparency in addition to the absorption and emission characteristics of any probes that are attached to the particles. Strongly-absorbing probes with a high quantum yield for fluorescent emission typically generate pulses of maximum amplitude.

In operation, at least one of the detectors receives a light pulse when a particle is illuminated by the excitation beam. Each interaction between a particle and the excitation beam is known as an "event." In the ideal case, a particle can be unambiguously identified from the characteristics of the detector pulses that are generated during an event. In certain samples, for example, it is possible to count and discriminate between monocytes, granulocytes and lymphocytes by measuring the relative magnitude of the small and large angle scattering signals. In other samples, the amount of DNA in cellular nuclei may be determined by measuring the shape of the fluorescent pulses that are emitted as the particles pass through the excitation volume.

With the exception of the flow cell and associated fluidics, capillary flow cytometers can be qualitatively similar to sheath flow instruments. The sample fluid is illuminated by a focused light source in an excitation volume and the light pulses that are emitted and scattered by the sample particles are collected by small and large angle optical systems that separate light pulses according to wavelength and direct them to detectors. Because of the inherent simplicity of capillary cytometer flow cells, they are easier to build and align than sheath flow instruments. However, the comparatively large cross section of the excitation volume in capillary flow instruments limits their measurement accuracy.

In both sheath and capillary flow cytometers, particles may be counted by comparing the shape of the detector pulses to predetermined criteria. In some cases, particles may be counted when the pulse height exceeds a threshold value. In others, plots of pulse height and width or area may be used to identify and count different particle types. Factors that may cause errors during the particle identification process include deviations from smooth laminar flow, spatial variations in particle velocity, spatial variations in the optical collection efficiency, the simultaneous illumination of multiple particles, or the formation of aggregates with the sample. The magnitude of these errors typically increase with the size of excitation volume and may be minimized in sheath flow instruments.

For many measurements, capillary systems provide adequate measurement accuracy and offer the following advantages with respect to sheath flow systems:

1. Reduced complexity and cost. Sheath flow cells are complex, expensive and difficult to align properly. Capillary flow cells are simpler, cheaper, and less prone to misalignment.

2. The sample fluid is drawn through the capillary by a pump, thereby facilitating the direct measurement of particle concentration in the sample fluid. In a sheath flow cytometer, the sample and sheath fluid are injected into the flow tube under pressure and particle concentrations are typically measured indirectly by introducing a sample fluid with a known particle concentration into the system.

3. The sheath fluid and associated fluidics are eliminated. The simpler fluidics of capillary flow instruments offer significant cost savings for certain common measurements where reductions in measurement accuracy are acceptable.

According to Shapiro (Practical Flow Cytometry, 4$^{th}$ Edition, Wiley, Hoboken, 2003), "the measurement precision of a cytometer is routinely characterized by accumulating a distribution of measured values of fluorescence or light scattering intensities from 'nearly identical particles' and computing the coefficient of variation (CV), which, expressed as a percentage, is 100 times the standard deviation for the measurement divided by the arithmetic mean, or average." Smaller CVs are associated with increased accuracy.

In a typical measurement, the count is increased when the amplitude of a pulse from a detector exceeds a predetermined threshold value. Variations in the pulse amplitudes produced by identical particles lead to counting errors and an undesirable increase of the CV for a measurement. CVs in prior art capillary cytometers typically exceed those of sheath flow instruments because of their larger excitation volumes and the emission of light from the particles far removed from the capillary axis.

In cytometry, the illumination of a single, isolated sample particle generates a single-peaked detector pulse, commonly referred to as a "singlet." The simultaneous illumination of two separate particles generates a detector pulse with two peaks, typically referred to as a "doublet." At high particle concentrations and in sample flows with a cross sectional dimension that is significantly greater than the particle cross section, the probability of simultaneously illuminating two particles is substantial.

Figure 4A:
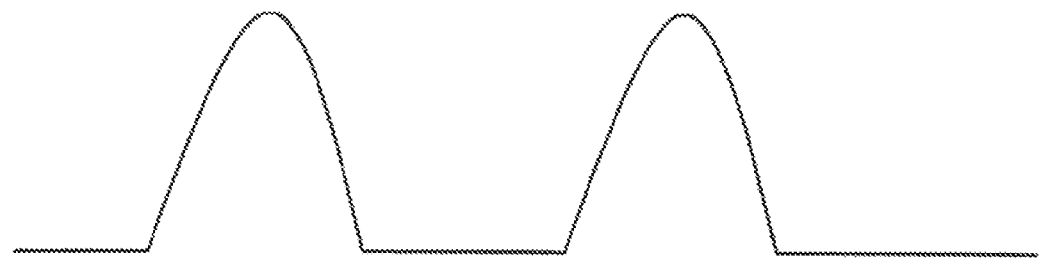
FIG. 4A is a plot representing single pulses produced when a first particle leaves an excitation volume before a second particle enters.
Figure 4B:
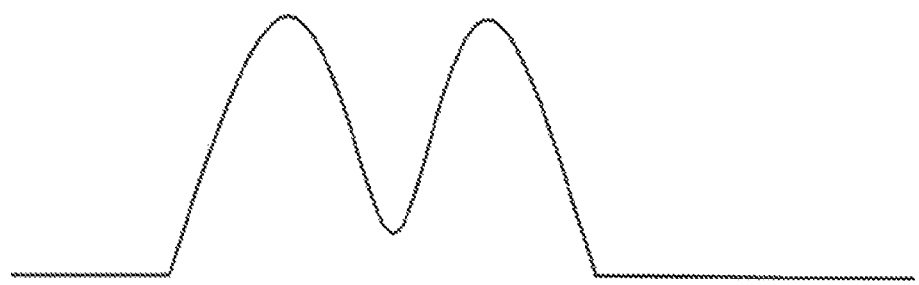
FIG. 4B is a plot representing a doublet pulse produced when portions of a first and second particle are simultaneously illuminated.
Figure 4C:
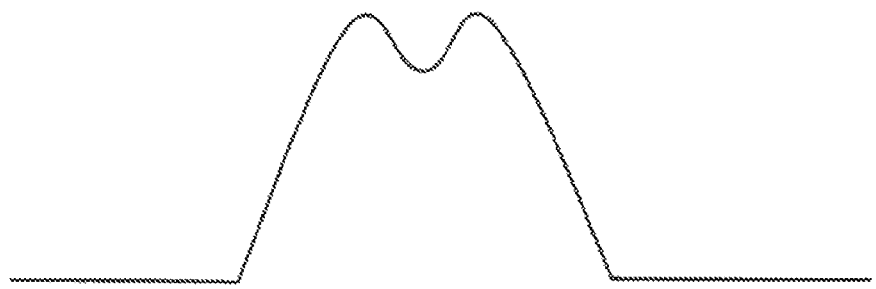
FIG. 4C is a plot representing a doublet pulse produced when large portions of a first and second particle are simultaneously illuminated.

FIG. 4A-4B are schematic representation of the changes in pulse shape that occur as the sample particle concentration is increased. At low concentrations, almost all events correspond to the illumination of single particles. Increasing the particle concentration or the cross sectional area of the capillary flow tube increases the probability of observing the doublet pulse shape. In FIG. 4A, a singlet pulse is generated by each particle since the first particle has left the excitation volume before the second particle enters it. In FIG. 4B, the second particle enters the excitation volume while a small portion of the first particle is still illuminated. In this case, the detector output does not return to zero between the pulses but there is a significant difference between the maximum and minimum pulse values. In FIG. 4C, the first and second particles pass through the excitation volume at almost the same time and the difference between the maximum and minimum pulse amplitudes are small.

Figure 5:
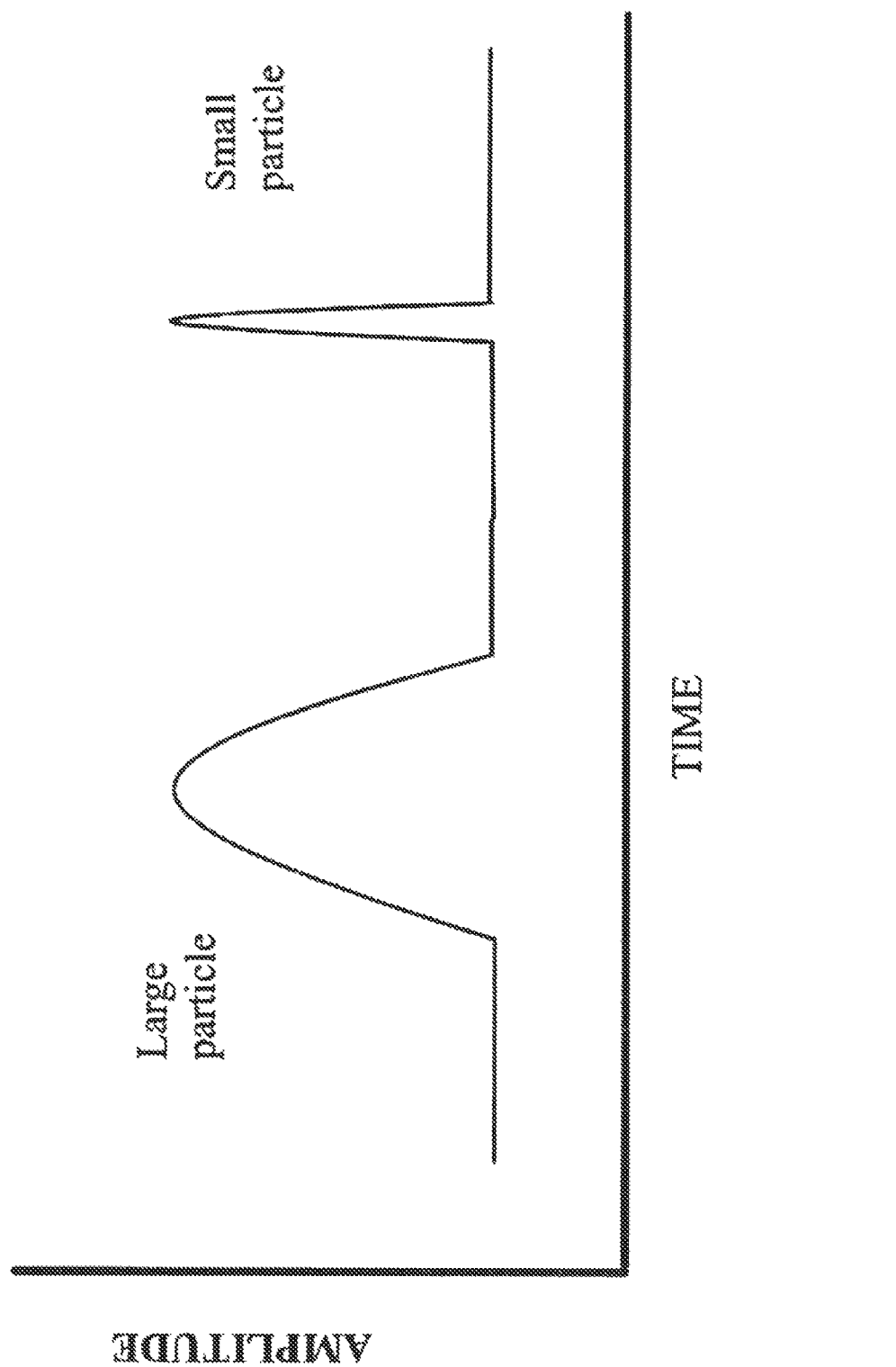
FIG. 5 is a plot illustrating the relationship between pulse shapes and particle sizes.
Figure 6:
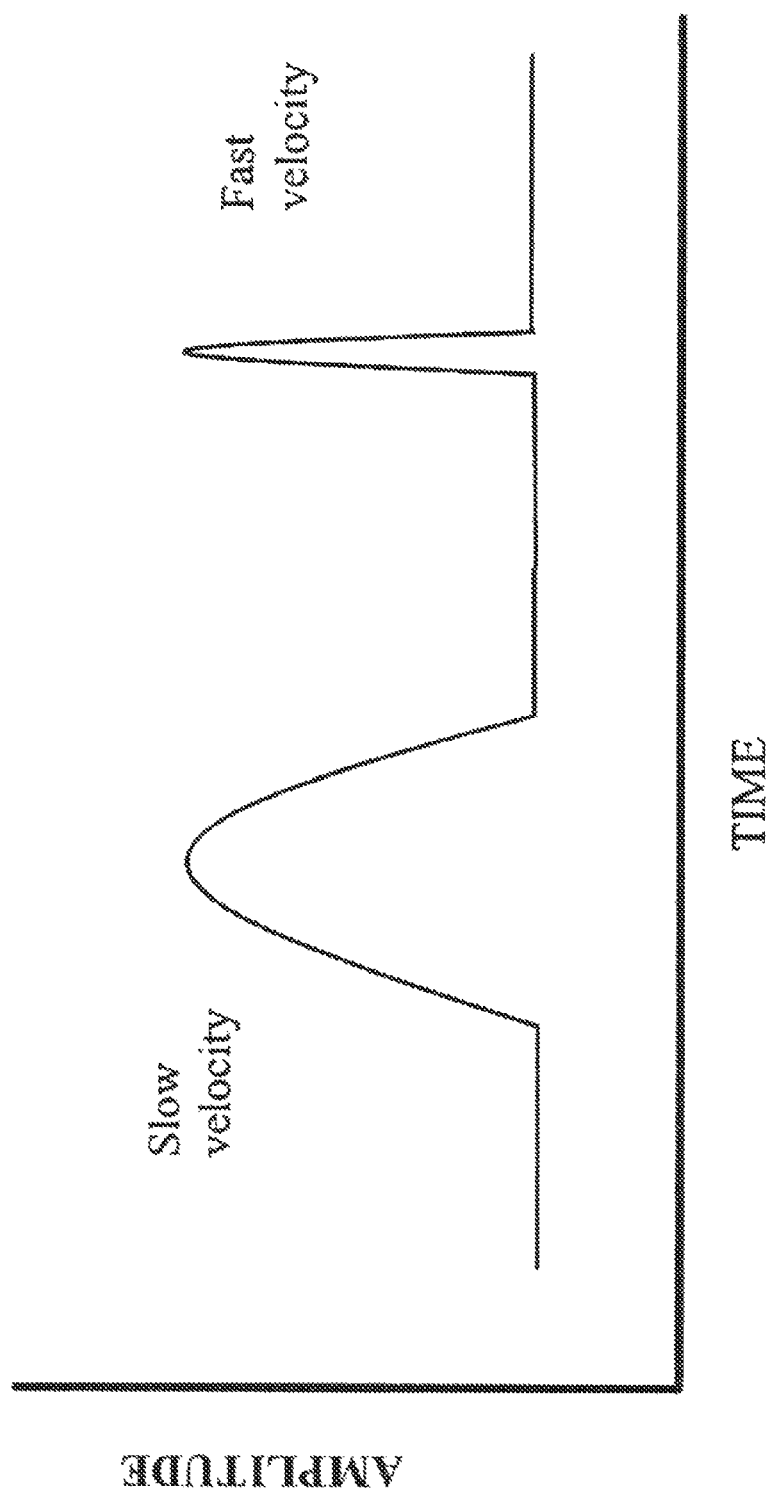
FIG. 6 is a plot illustrating the relationship between pulse shapes and particle velocities.

In certain samples, cells, cellular fragments and other debris may clump together to form aggregates. These aggregates typically have dimensions that are different from the dimensions of the particles of interest. In a sheath flow cytometer in which particles pass through the excitation volume with approximately the same velocity, the pulse width is strongly correlated to particle size as illustrated in FIG. 5. Thus, doublets and aggregate pulses may be identified and eliminated from analysis using the pulse and area/width techniques as described in Wersto et al., Cytometry 46:296-306 (2001), the disclosure of which is incorporated herein by reference for general information. This type of analysis cannot however be performed in conventional capillary flow cytometers since pulse widths are also strongly-correlated to particle velocity as illustrated in FIG. 6. In such systems, the pulse shape variations caused by the radial variation of flow and particle velocities effectively masks the pulse shape differences between single particles and aggregates or doublets.

In some embodiments, the concentration of particles in the sample can be adjusted so that the probability of illuminating more than two particles is insignificant and doublets are rarely detected. In some instances, aggregate formation is difficult to prevent in certain biological samples.

In some embodiments, the accuracy of capillary flow systems may be improved by concentrating the particles in a small region near the capillary axis. In this case, the performance of the capillary flow cytometer may approximate that of a sheath flow instrument. U.S. Pat. No. 6,710,871 B1 to Goix, for example, describes a capillary flow cytometer system in which a magnetic field is used to force magnetically-charged particles to flow within a restricted cross sectional area of the capillary. US Patent Application Publication No. 2006/0021437 entitled "Ultrasonic analyte concentration and application in flow cytometry," by Kaduchak, et al. describes ultrasonic techniques for concentrating particles near the capillary axis. U.S. Pat. No. 6,710,871 B1 and US Patent Application Publication No. 2006/0021437 are incorporated herein by reference in their entirety.

In some embodiments, the derivatives of the pulses produced when sample particles flow through an excitation volume in a flow cytometer are computed in real time using numerical techniques. When the cytometer is operated within typical ranges of particle concentration and volume flow rate, particle velocities may be calculated from the derivatives and used to correct individual pulse shapes so they closely approximate those in a uniform velocity flow. Calculated velocities may also be used to uniquely identify the pulses produced by a single particle as it flows through a capillary instrument with multiple excitation volumes. In some embodiments, the number of zero-crossings in the calculated derivative of a pulse may be used to differentiate between doublet and singlet pulses.

In one specific embodiment, the invention provides a method of analyzing pulses from a flow cytometer in which particles in a fluid pass through an excitation volume of an electromagnetic radiation and interact with the electromagnetic radiation to generate signals in the form of pulses. A time-dependent pulse indicative of the characteristics of one or more particles passing through the excitation volume of the electromagnetic radiation is generated. A measurement window is determined by selecting a portion of the pulse with a starting point and an ending point above a predetermined value. A first derivative of the pulse with respect to time over the measurement window is calculated.

Figure 7:
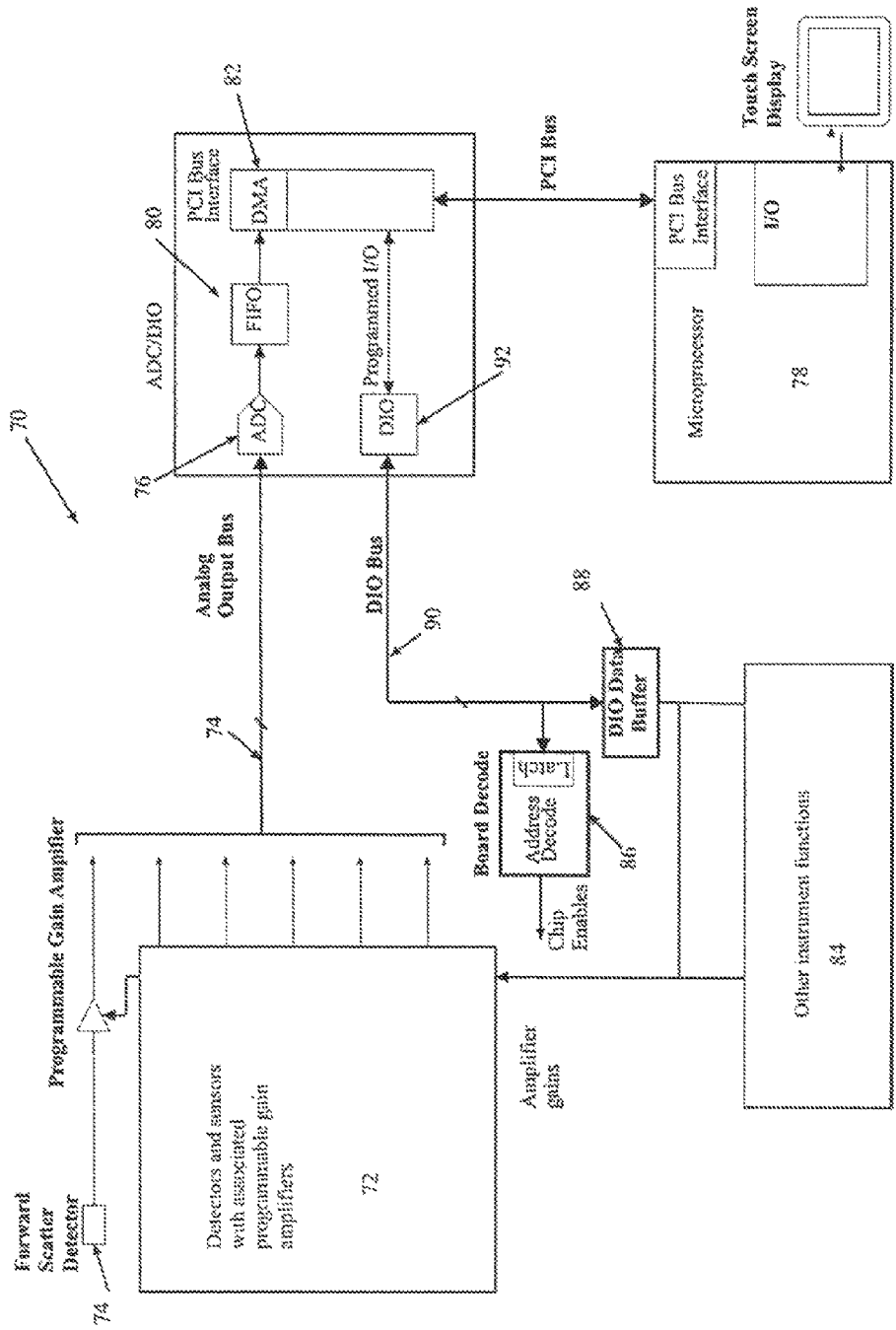
FIG. 7 is a block diagram of an electronic system that may be used to implement the method of the invention.

FIG. 7 is a block diagram of an electronic system 70 that may be used to calculate the derivative of the signals from a detector in a flow cytometer. The flow cytometer may be a capillary flow cytometer. Functional blocks on the diagram utilize technology and components that are well-known in the electronic and digital signal processing art.

Referring to FIG. 7, light pulses are received by a detector 72, generating electronic signals that are amplified by a programmable gain amplifier and transported by the analog output bus 74 to an analog to digital converter (ADC) 76. The analog bus 74 may also carry signals from other amplified detectors 78, pressure transducers, or other sensors. By way of example, the analog bus 74 may carry four or five amplified signals to the ADC 76.

The ADC 76 may, for example, digitize the signals at a sampling rate of 40 kHz with a resolution of 16 bits. Interleaved digital data from the ADC 76 may be stored in the memory of a microcomputer 78. By way of example, the microprocessor may be an Eden 1 GHz Processor with 512 megabytes of random access memory. A FIFO buffer 80 and direct memory access module (DMA) 82 may be used to efficiently multiplex the data transfer process with other processes that are concurrently performed by the microcomputer 78.

Digital data from the computer memory (not shown), that may include operating parameters for the other instrument components 84, detector voltage settings and gain settings for the forward scattering detector programmable amplifier and other programmable amplifiers, is transported from the computer memory to a board decoder 86 and digital input/output (DIO) buffer 88 by a DIO bus 90 under the control of a DIO bus controller 92. Amplifier settings and digital control settings for other components are sent from the DIO buffer 88 to individual instrument components. Analog control signals are generated from data transported by the DIO bus 90 to the Board Decode module 86.

The interleaved ADC data is read from memory by the microcomputer 78 and de-interleaved into buffers—one for each measured parameter. By way of example, the data from the detector 72 may be stored in a single, de-interleaved buffer. Alternatively, data from additional detectors may be stored in additional buffers.

An upsampling filter is typically applied to the de-interleaved data. Suitable filters include 8× and 16× upsampling lowpass filters that are well known in the prior signal processing art. Such filters provide improved interpolation between samples, improved estimation of the peak value, and some high-frequency noise rejection.

To calculate the derivative of a pulse, a measurement window may be defined by determining the points where the ratio of pulse intensity to the peak intensity is equal to a predetermined value. The derivative is then calculated for each data point within this window.

Calculation of the derivative may be performed by the microprocessor 78 using any prior art numerical technique that is both fast and stable in the presence of the noise signals commonly generated by flow cytometer detectors. For example, the derivative may be calculated using the Savitsky-Golay method as described in "Smoothing and Differentiation of Data by Simplified Least Squares Procedures," Abraham Savitzky and Marcel J. E. Golay, *Analytical Chemistry*, 36, pp. 1627-1639 (1964), the disclosure of which is incorporated herein by reference in its entirety. This method sequentially performs a local polynomial regression around each data point in the derivative buffer and uses the polynomial fit to estimate the first derivative of the original signal. It combines data smoothing (via the regression) with a derivative estimation filter.

For example, a 9-point Savitsky-Golay filter (n=9) was used in combination with a second degree polynomial (k=2). A value proportional to the derivative at a specific data point was calculated by sequentially multiplying ordered sets of 9 data points by the following coefficients {86, −142, −193, −126.0, 126, 193, 142, −86}. The first calculation used data points 1-9, the second calculation used data points 2-10, the third calculation used data points 3-11 etc., until scaled derivative values for all data points within a predetermined calculation window were computed. Input data points were retrieved from the de-interleaved input buffer and the results of the derivative calculation stored in a derivative output buffer.

Figure 8:
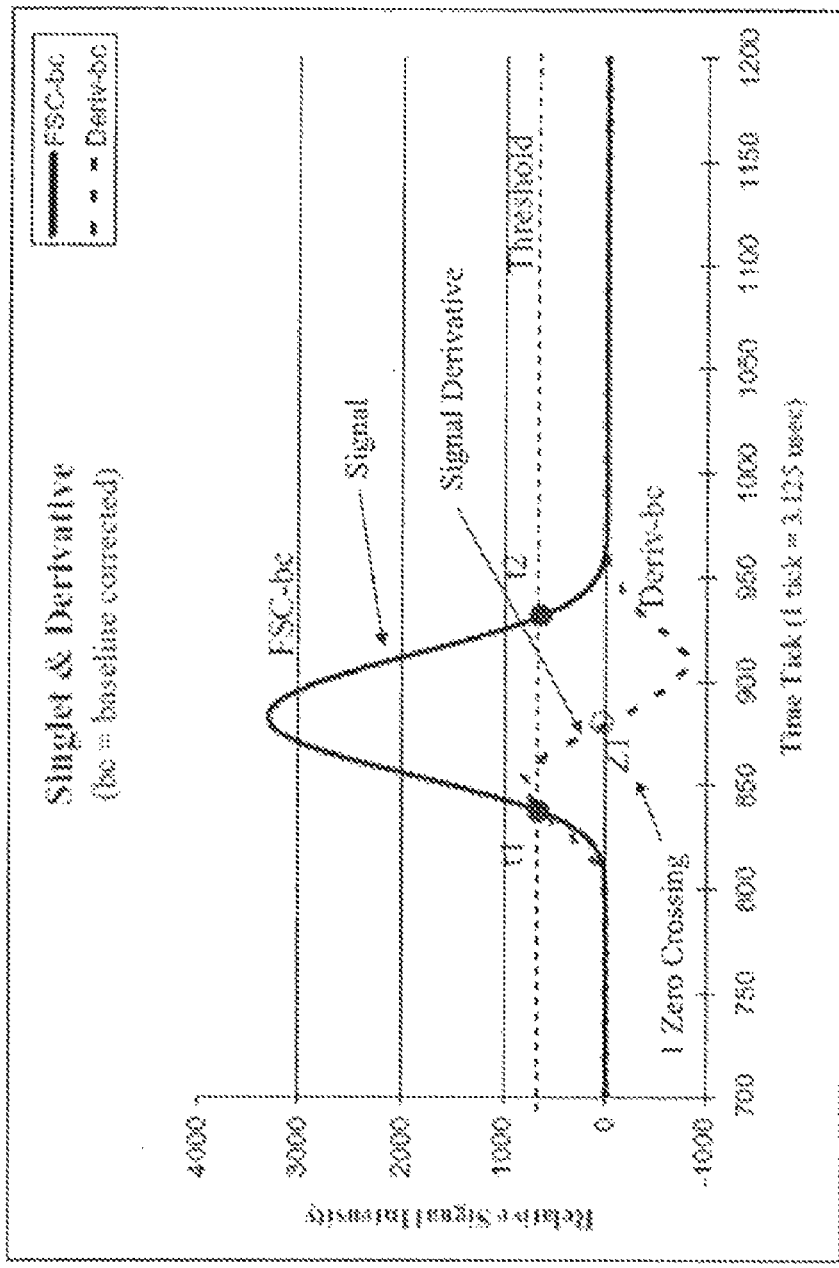
FIG. 8 is a plot illustrating a time dependent signal and a first derivative of the time dependent signal when a single particle bead is illuminated.

FIG. 8 illustrates a pulse shape and a derivative pulse shape computed in accordance with one embodiment of the invention. In FIG. 8, the time dependent signal and the first derivative of the time dependent signal were produced by the forward scattering channel of a capillary flow cytometer available from Guava Technologies, Inc., Hayward, Calif. $T_1$ and $T_2$ are starting and ending points that the detector signal crosses a preset threshold level. The pulsewidth is defined by the difference between $T_1$ and $T_2$. $Z_1$ is the first derivative zero crossing. It is coincident with the pulse signal maximum.

The Savitsky-Golay filter is but one of a large number of suitable numerical methods for calculating the first derivative from a digital data set. In alternative embodiments, the derivative may be approximated using alternative numerical techniques with suitable speed, accuracy and stability.

In some embodiments, the particle velocity may be calculated from the derivative data in a measurement window defined for example by the ¼ intensity points of the pulse. Maximum and minimum values of the derivative in the measurement window are identified and the particle velocity estimated from the following equation:

$$V = \frac{\alpha \cdot k}{P}$$

where V is equal to the particle velocity, $\alpha$ is the maximum value of the derivative $\alpha$=max[(Abs(derivative))], Abs is the absolute value function, k is a scaling factor that depends on shape of the excitation laser beam, and P is the pulse height. For a Gaussian laser beam $$k = \frac{\sqrt{e} \cdot BW}{4},$$

where BW is the $1/e^2$ width of the beam. The above applies for particles small compared to the BW. Sometimes noise or other effects modulate the pulse shape and it is advantageous to calculate $\alpha$ from an average of derivative maxima and minima. In a preferred embodiment, $\alpha$ is calculated from the formula:

$$\alpha = \frac{\text{Abs}(\max) - \text{Abs}(\min)}{2}.$$

However, there are many other methods for calculating $\alpha$.

Derivative-Based Velocity Correction for Pulse and Area/Width Calculations

Flow cytometers are often used for DNA cell cycle analysis. In this measurement, the relative fraction of sample cells in the G1, S, and G2+M phases of the cell cycle are determined by staining them with a DNA-specific dye and passing them through the excitation volume of a flow cytometer. The size and amount of DNA in the nucleus of a given particle is dependent on its cell cycle stage and, hence, the pulses produced by particles in different stages have different shapes. Pulses may be analyzed according to their amplitude, area, and width using well-known techniques as described in Wersto et al., "Doublet Discrimination in DNA Cell-Cycle Analysis," Cytometry 46:296-306 (2001), the disclosure of which is incorporated herein by reference in its entirety. Alternative techniques for pulse shape analysis are described in U.S. Pat. Nos. 4,021,117 and 3,938,038, the disclosures of which are incorporated herein by reference in their entirety. Collectively, the prior art electronic and numerical signal processing techniques for pulse shape analysis in sheath flow cytometers will be described as "pulse and area/width techniques."

The accuracy of cell cycle measurements is degraded when the sample contains a non-zero concentration of aggregate particles that have an excess of DNA material. In sheath flow cytometers, aggregate pulses may be identified using pulse and area/width techniques. These techniques rely on the fact that aggregates typically have sizes and DNA amounts that are different from single cells in the various stages of the cell cycle.

In a sheath flow cytometry system, measurements of area and width may be made directly from the individual pulses because the cells are passing through the laser beam at a constant velocity. In a capillary flow cytometer, the particle velocity is a function of radial distance from the capillary axis. In a typical capillary system, for example, the velocity of the most distant particles may be one third of the velocity of the particle traveling near the capillary axis, and area and width of individual pulses are strongly dependent on the radial distance of the particle from the flow tube axis.

Using the velocity measurement method of the invention, the velocity of the particle may be calculated from the derivative of the pulse and the particle shape may be velocity-corrected accordingly. Once the velocity correction has been performed, the pulses may be analyzed using the conventional pulse and area/width techniques. Errors associated with the analysis of the velocity-corrected pulses are comparable to those obtained in the analysis of uncorrected pulses in a sheath flow instrument.

Velocity correction may be simply accomplished by multiplying the values of the width and area of a given pulse by the calculated particle velocity. For example, the uncorrected pulse width is determined by measuring the temporal width of the calculation window (time between the ¼ max points of the input pulse) and the area determined by integrating the uncorrected intensity data over the calculation window. Velocity correction to both values is accomplished by multiplying the uncorrected data by the calculated velocity.

Derivative-Based Doublet Discrimination

Figure 9:
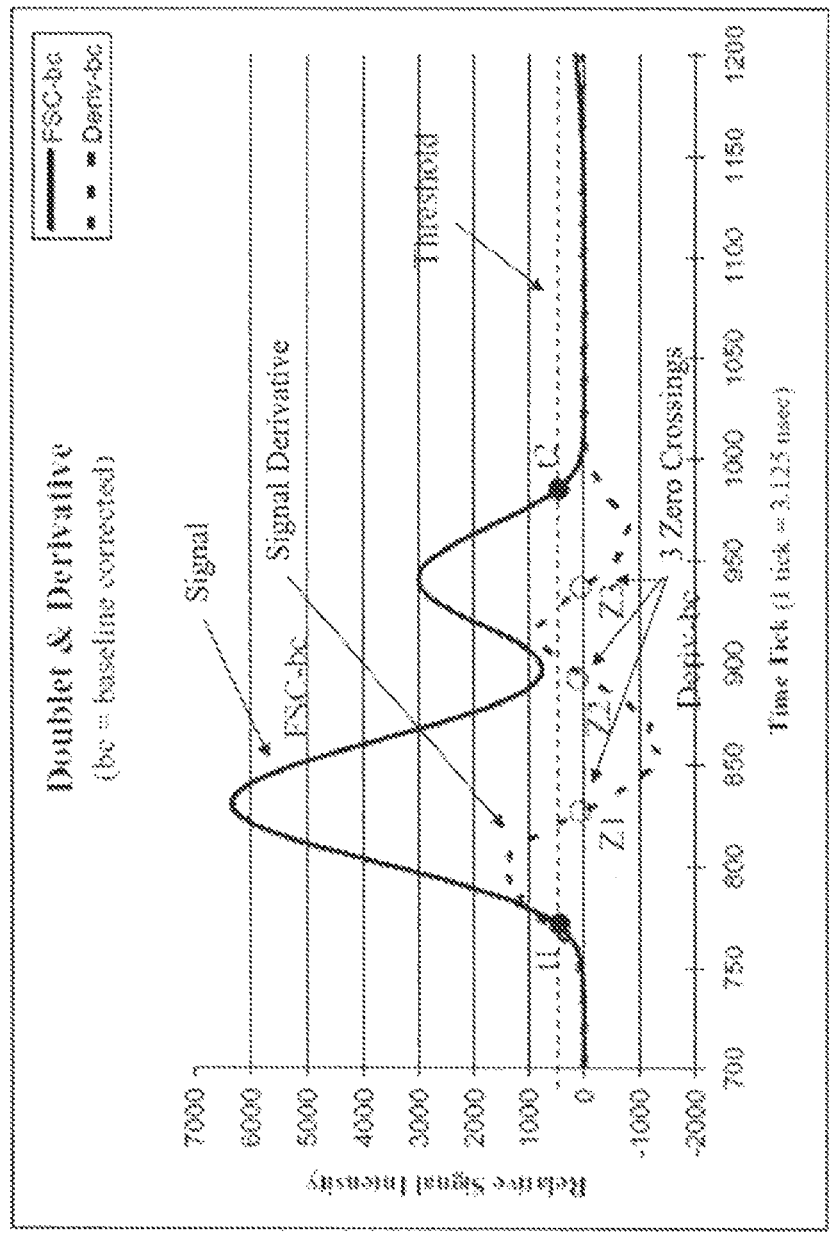
FIG. 9 is a plot illustrating a time dependent signal and a first derivative of the time dependent signal when two particle beads are simultaneously illuminated.

Due to the comparatively large cross sectional area of the flow tube in a typical capillary flow cytometer, there is often a non-zero probability of simultaneously illuminating more than one sample particle at a time. FIG. 8 is a plot of a detector signal and first derivative of the detector signal generated by an isolated single particle. FIG. 9 is a plot of a detector signal and the first derivative of the detector signal that was generated by the simultaneous illumination of two particles.

The representative signals in FIG. 8 and FIG. 9 were produced by a forward scatter detector of a capillary flow cytometer, available from Guava Technologies, Inc., California. A sample containing Guava Check® beads was excited. Guava Check® beads are provided as a concentrated fluorescent bead suspension of known concentration. In use, the beads may be diluted to yield a bead suspension of known concentration. The duration of the singlet and doublet pulses are the difference between the times $T_1$ and $T_2$ when the signals cross a preset threshold. The derivative signals cross zero at each maximum and minimum—once for the singlet pulse and three times for the doublet pulse. The derivative zero-crossings are labeled $Z_1$ in FIG. 8, and $Z_1$, $Z_2$ and $Z_3$ in FIG. 9. In the rare event that more than two particles are illuminated simultaneously, the derivative signal is expected to cross zero $(2n-1)$ times where n is the number of simultaneously illuminated particles.

Doublet and singlet pulses may be separated by calculating the derivative of an input pulse using the techniques of the invention and determining the number of times the derivative is approximately equal to zero. Singlet pulses have a single zero and doublets have 3.

Alternatively, doublet pulses and singlet pulses may be separated by calculating the maximum derivative value and the width for each pulse. For a given particle size, the maximum derivative of the rising edge of a singlet pulse and the width of the singlet pulse scale with velocity in such a way that the ratio of the two parameters is approximately independent of the particle velocity. In the case of doublet pulses, however, the rising edge derivative varies with velocity in much the same way as with singlet pulses but the pulsewidth is increased over the singlet case by an amount proportional to the separation between the two particles in the direction of the flow. Therefore, doublet and singlet pulses may be identified by calculating the pulsewidth to maximum derivative ratio. Singlet pulses correspond to pulsewidth-to-derivative ratios that are smaller than a predetermined doublet threshold value. Real-time derivative calculations according to the present invention may be used to calculate the maximum value of the leading-edge derivative and the pulsewidth-to-derivative ratio used to discriminate between doublet and singlet pulses.

Velocity-Based Particle Tracking in Multi-Source Flow Cytometers

In certain measurements, it is desirable to illuminate sample particles with two or more excitation wavelengths. This is typically accomplished by focusing the output beams from different lasers at different points along the flow so that separate excitation volumes are created for each laser. The light pulses from each volume are collected and separated according to wavelength and angle by different optical systems.

In cases where measurements are made on a single particle in two or more excitation volumes, it is necessary to correlate the pulses emitted in each excitation volume with the single particle that produces them. In a sheath flow instrument where all particles travel at approximately the same velocity, the correlation may be accomplished by setting time gates that correspond to the transit time between different excitation volumes. For example, the rising edge of the pulse generated by a particle in an upstream volume may be used to time gate the data collection in downstream excitation volumes in such a way that the pulses generated by the triggering particle are identified and recorded. This approach however may not be used in a conventional capillary flow cytometer where the particle velocity is a strong function of distance from the capillary axis. In the best case, the time required for a particle to travel between excitation volumes is variable and, in the worst case, the order in which two particles pass an excitation volume is reversed as the particles travel downstream.

Figure 10:
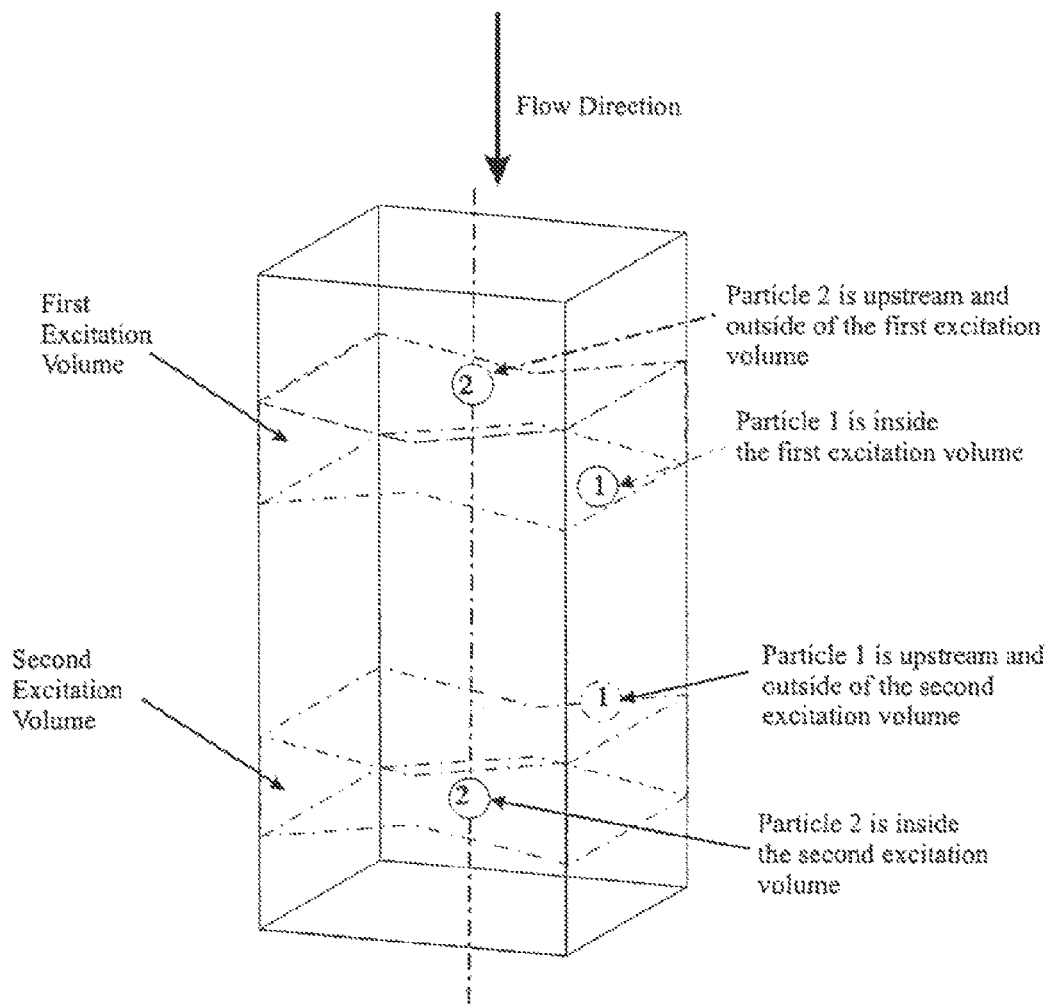
FIG. 10 is schematic illustrating two particles passing through a capillary flow cell having two excitation volumes.

FIG. 10 is a schematic illustration of two particles traveling through a capillary flow cell with two excitation volumes. Particle No. 1 travels near the wall of the capillary tube at a first velocity while Particle No. 2 travels near the axis at a second velocity that is substantially greater than the first. In the illustration, Particle No. 1 travels through the first excitation volume before Particle No. 2, but the faster moving Particle No. 2 overtakes and passes Particle No. 1 as they flow between the excitation volumes. Consequently, Particle No. 2 travels through the second excitation volume (and all other downstream excitation volumes) before Particle No. 1. A simple electronic time gate, triggered by the rising edge of the pulses produced by particles traveling through the first excitation volume may miss a fraction of the pulses in the second excitation volume and, in those cases where a pulse is recorded in the second volume, it is impossible to determine if it is produced by the same particle that triggered the gate.

The claimed invention may be used to calculate the velocity of a particle as it flows through the first excitation volume and the time required for the particle to reach excitation volumes that are downstream from the first. Pulses produced by a particle as it travels through the downstream excitation volumes may be correlated to the pulses in the first volume using the velocity data. Because the interval between a triggering pulse and a time gate is accurately calculated from the velocity of the triggering particle, the probability of missing pulses or inaccurately associating the pulses in downstream excitation volumes with the triggering pulses is very low.

Since the velocity of the particles is approximately constant as they flow through the excitation volumes, the pulses produced by a particular particle may also be identified by performing velocity calculations for the pulses produced in all zones. If the rising edge of a pulse in the first excitation volume triggers a measurement window in a second excitation volume that is wide enough to include all possible transit times between the first and second excitation volumes, pulses produced during the window with approximately equal derivative values (velocities) may be deemed to be generated by the same particle.

EXAMPLE 1

Figure 11A:
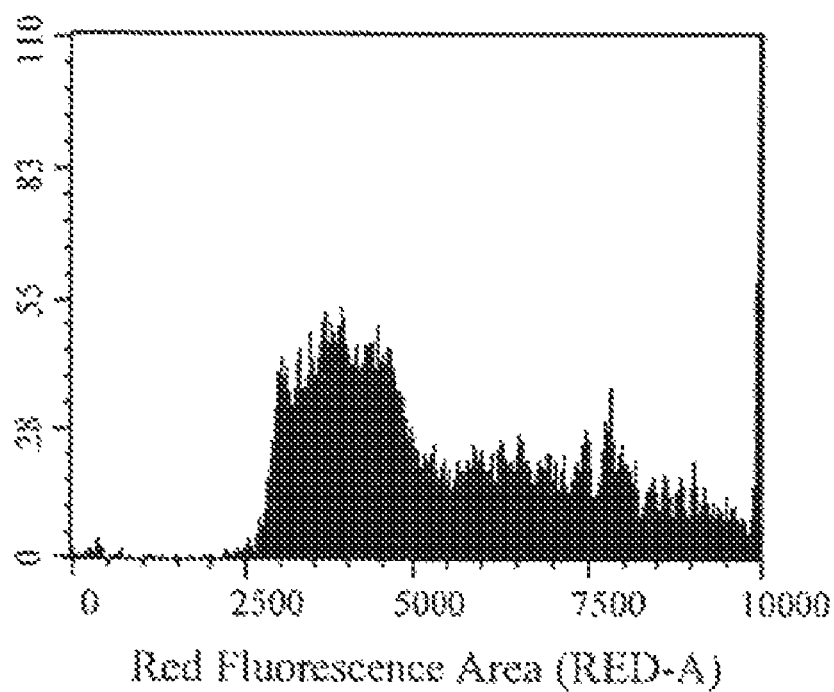
FIG. 11A is a plot of uncorrected area data generated by passing mammalian cells that were stained with propidium iodide (PI) through a capillary cytometer at an average volume flow rate of 125 µl/sec.
Figure 11B:
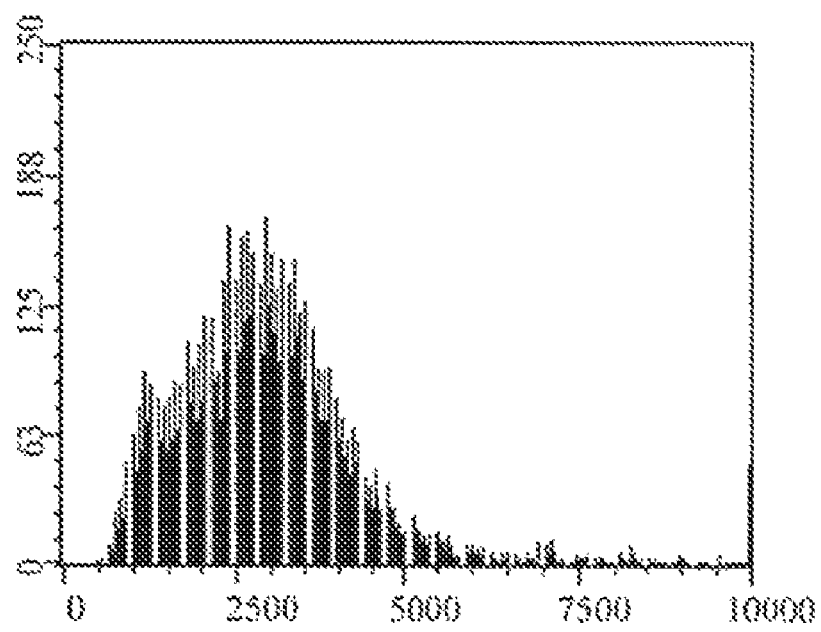
FIG. 11B is a plot of uncorrected width data generated by passing mammalian cells that were stained with propidium iodide (PI) through a capillary cytometer at an average volume flow rate of 125 µl/sec.

This example illustrates velocity correction of area and width data in accordance with the present invention. FIGS. 11A-11B illustrate uncorrected area and width data from a capillary cytometer, EasyCyte®, available from Guava Technologies. This data was generated by passing mammalian cells that were stained with the nuclear DNA stain, propidium iodide (PI) through the instrument at an average volume flow rate of 125 μl/sec.

Propidium iodide (PI) was used as a nuclear DNA stain in the cell cycle assay to discriminate cells at different stages of the cell cycle. Resting cells (G0/G1) contain two copies of each chromosome. As cells begin cycling, they synthesize chromosomal DNA (S phase). Fluoresce intensity from the DNA intercalating dye, PI, increases until all chromosomal DNA has doubled (G2/M phase). At this state, the G2/M cells fluoresce with twice the fluorescence intensity of the G0/G1 population. The G2/M cells eventually divide into two cells.

For identically-sized particles in different stages of the cell cycle, the width data in FIG. 11B should be sharply peaked and the area data in FIG. 11A should have a qualitative form showing DNA contents in different stages. Because the particles traveled through the excitation volume with differing velocities, however, the uncorrected width histogram in FIG. 11B forms a broad peak and the shape of the uncorrected area histogram in FIG. 11A is not in a qualitative form showing DNA contents in different stages.

Figure 12A:
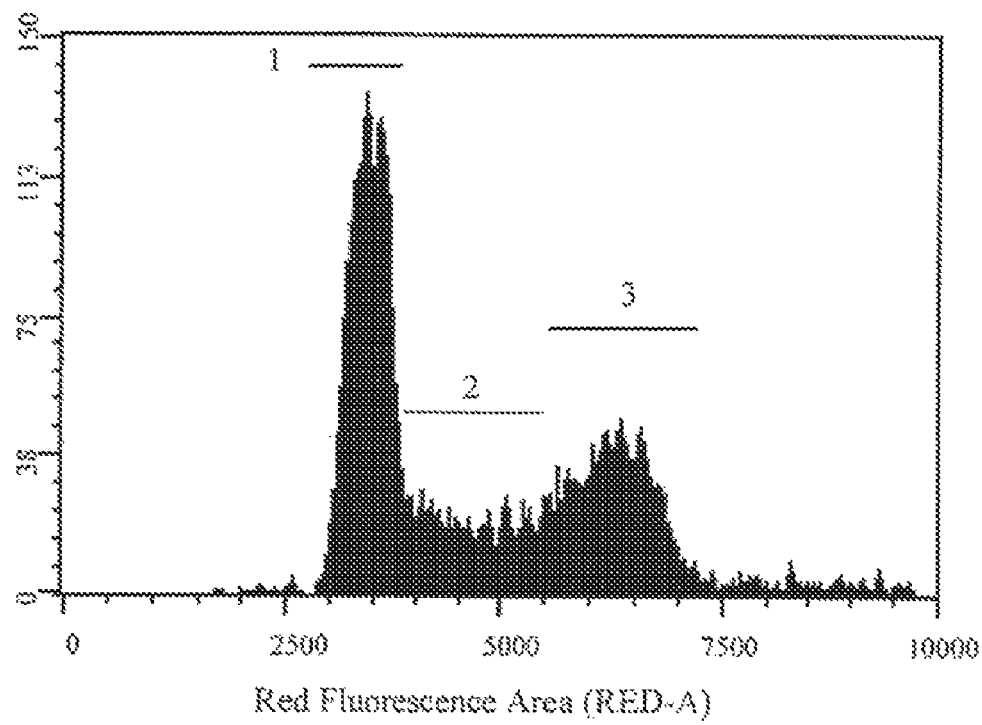
FIG. 12A is a plot of corrected data of FIG. 11A after real-time velocity correction according to one embodiment of the present invention.
Figure 12B:
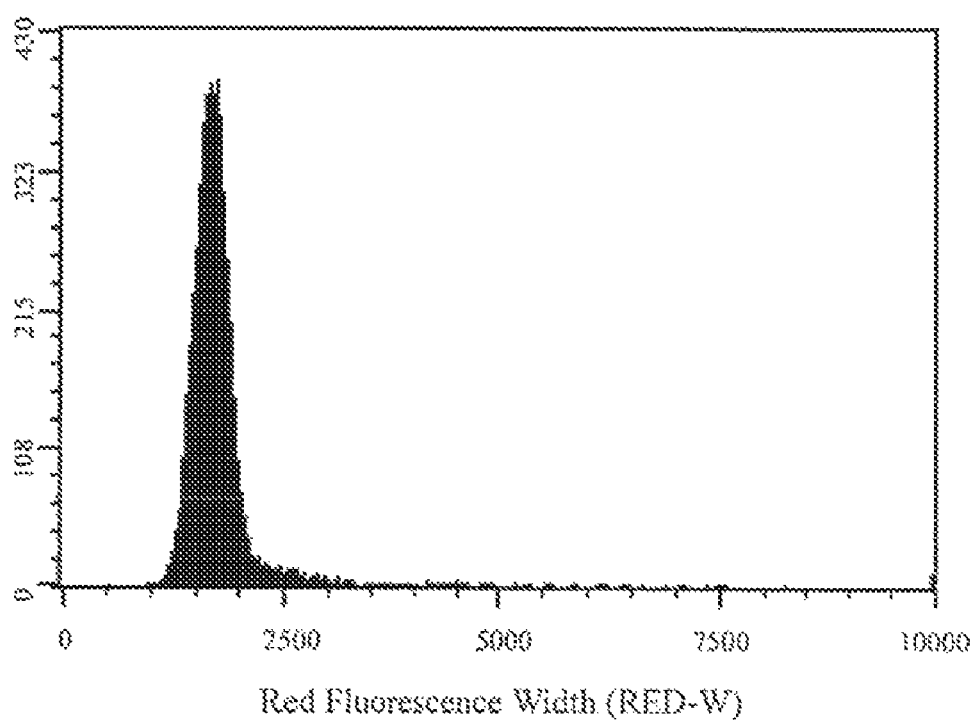
FIG. 12B is a plot of corrected data of FIG. 11B after real-time velocity correction according to one embodiment of the present invention.

FIGS. 12A-12B show corrected data of FIGS. 11A-11B after real-time velocity correction according to the present invention. The histogram of the velocity-corrected width data in FIG. 12B is a narrow, well-defined peak and the histogram of the velocity-corrected area data in FIG. 12A qualitatively shows the cycle stages. The velocity corrected data of FIGS. 12A-12B may subsequently be analyzed using the techniques of Wersto et al. to eliminate doublet and aggregate-generated pulses.

It will be obvious to those skilled in the flow cytometry art that the real time calculation of derivatives and particle velocities according to this invention may be used for applications other than those detailed in this disclosure. Furthermore, it is obvious that the derivative may be calculated using a wide range of numerical techniques without deviating the spirit of the invention. For example, the invention may be practiced by using forms of the Savitsky-Golay filter corresponding to polynomial fits of higher degree and/or the use of more data points per calculation as described in "Smoothing and Differentiation of Data by Simplified Least Squares Procedures," Abraham Savitzky and Marcel J. E. Golay, *Analytical Chemistry*, 36, pp. 1627-1639 (1964).

Those skilled in the digital data processing or flow cytometry arts will realize that the invention may also be practiced using electronic components that are different than those shown in FIG. 7. In particular, the calculation of the pulse derivative may be performed by a dedicated digital signal processing circuit that is controlled by a microprocessor or alternative control unit. Numerous component combinations, known to the digital electronics and signal processing art, may be used to convert the analog signals to digital data and calculate the derivative of the digital data. The various electronic components may be housed within the flow cytometry instrument or connected to it using appropriate cables. For example, the ADC/CIO Card and Microprocessor functions shown in FIG. 7 may be housed in two separate electronic chassis that are physically separate from each other and from a capillary flow cytometer.

What is claimed is:

1. A method of analyzing pulses of a capillary flow cytometer comprising:
    passing a fluid containing particles through an excitation volume in a capillary flow cytometer, said excitation volume being defined at least partially by a light beam and a portion of a capillary illuminated by the light beam;
    generating a time-dependent pulse as one or more particles pass through the excitation volume;
    computing a first derivative of the pulse with respect to time;
    calculating a velocity of the one or more particles passing through the excitation volume using the computed first derivative; and
    correcting the time-dependent pulse using the calculated velocity.

2. The method of claim 1 wherein said passing step comprises passing a liquid sample containing the particles through the excitation volume.

3. The method of claim 1 wherein said excitation volume is defined at least partially by a focused light beam having a single peak.

4. The method of claim 1 wherein the generating step comprises generating a time-dependent pulse indicative of scatter light from the one or more particles interacting with the light beam when passing through the excitation volume.

5. The method of claim 1 wherein the generating step comprises generating a time-dependent pulse indicative of fluorescence from the one or more particles interacting with the light beam when passing through the excitation volume.

6. The method of claim 1 wherein said correcting step comprises multiplying an area or a width of the time-dependent pulse by the calculated velocity.

7. The method of claim 1 further comprising the steps of determining a number of times the first derivative has a zero value, and identifying a singlet or doublet pulse using the number of times.

8. The method of claim 1 further comprising identifying a maximum of the first derivative, calculating a ratio of the identified maximum to a width of the pulse, and differentiating a singlet pulse from a doublet pulse using the calculated ratio.

9. An apparatus for analyzing particles comprising:
   a capillary tube adapted to be filled by a fluid containing particles to be analyzed;
   a source of light;
   an optical system operable to direct a light beam from the source of light to a portion of the capillary tube forming an excitation volume;
   means for causing the fluid to pass through the excitation volume in which particles to be analyzed interact with the light beam to scatter light and/or emit fluorescence;
   means for detecting the fluorescence in form of pulses; and
   means for computing a first derivative of the pulses with respect to time over a measurement window.

10. The apparatus of claim 9 further comprising means for detecting scatter light in form of pulses, and means for calculating a first derivative of the scatter light pulses with respect to time over a measurement window.

11. The apparatus of claim 9 further comprising means for calculating a velocity of particles using the computed first derivative of the pulses.

12. The apparatus of claim 9 wherein said optical system is adapted to direct a focused light beam to the portion of the capillary tube.

13. The method of claim 1 wherein the particle containing fluid is a liquid fluid.

14. The method of claim 1 wherein the light beam is a single Gaussian beam produced by a laser.

* * * * *